US005586556A

United States Patent [19]
Spivey et al.

[11] Patent Number: 5,586,556
[45] Date of Patent: Dec. 24, 1996

[54] PACEMAKER AND HEART MONITORING AND DATA TRANSMITTING DEVICE AND METHOD

[75] Inventors: Thomas R. Spivey, West Linn; Byron G. Zahler, Portland, both of Oreg.

[73] Assignee: T Z Medical, Inc., Lake Oswego, Oreg.

[21] Appl. No.: 438,688

[22] Filed: May 11, 1995

[51] Int. Cl.⁶ ........................................................ A61B 5/04
[52] U.S. Cl. ............................................ 128/697; 128/704
[58] Field of Search ....................................... 128/697, 904

[56] References Cited

U.S. PATENT DOCUMENTS

| D. 341,659 | 11/1993 | Homayoun . |
| 3,938,507 | 2/1976 | Sarnoff . |
| 4,531,527 | 7/1985 | Reinhold . |
| 4,862,896 | 9/1989 | Reinhold . |
| 4,889,134 | 12/1989 | Greenwold . |
| 4,938,229 | 7/1990 | Bergelson . |
| 4,958,641 | 9/1990 | Digby . |
| 4,977,899 | 12/1990 | Digby . |
| 5,012,814 | 5/1991 | Mills . |
| 5,111,396 | 5/1992 | Mills . |
| 5,172,698 | 12/1992 | Stanko ................................. 128/903 |
| 5,191,891 | 3/1993 | Righter . |
| 5,226,425 | 7/1993 | Righter . |
| 5,433,208 | 7/1995 | Lundstrom et al. ................. 128/696 |

Primary Examiner—William E. Kamm
Assistant Examiner—Scott Getzow
Attorney, Agent, or Firm—Robert L. Harrington

[57] ABSTRACT

A pacemaker and heart monitoring and transmitting device connects by telephone to a remote receiving station by both cradle coupling to a patient telephone handset and hands-free communication modes. The device collects an analog patient signal, including electrical EKG activity and pacemaker stimulation pulse width information, and applies such analog signal to a microcontroller executing conversion to digital form and application of digital signal processing (DSP) to produce a digitally generated tone representing patient EKG and stimulation pulse width information for delivery by telephone connection to a remote receiving station. The device further reacts to DTMF tones originating from the remote station to alter operation including increase or decrease in speaker volume, activation of a patient alert signal, initiation of hands-free mode, and a variety of other command features.

13 Claims, 10 Drawing Sheets

PACEMAKER AND HEART MONITORING AND DATA TRANSMITTING DEVICE AND METHOD

FIELD OF THE INVENTION

The present invention relates generally to heart monitoring devices, and particularly to devices monitoring heart and pacemaker activity and transmitting such data to a remote station for evaluation.

BACKGROUND OF THE INVENTION

A pacemaker implanted in a patient assists in maintaining patient heart rate. The pacemaker, a battery-powered device, detects the natural heart rate and supplements the natural heart rate when necessary, e.g., stimulating additional heartbeats to maintain a given heart rate. Pacemakers provide a variety of functions specific to a given patient's condition, e.g., stimulating the atrium, ventricle or both chambers. For purposes of the present invention, however, the pacemaker stimulates individual heartbeats when required and entirely "captures" the heart when stimulating every heartbeat. Doctors intermittently monitor the condition of patients and of implanted pacemakers to ensure a stable patient condition and a working and reliable pacemaker.

A pacemaker monitor transmitter (PMT), used by patients with an implanted pacemaker, determines patient heart and pacemaker condition. The pacemaker monitor transmitter connects to the patient with electrodes and monitors the patient's heart electrical activity (EKG) as well as certain other pacemaker functions. Some pacemakers, for example, respond to a magnetic field by "capturing" the heart and establishing a heartbeat at a given "magnetic" rate, i.e., bypasses demand mode. A patient triggers a pacemaker into such "magnetic" mode by placing a strong magnet near the pacemaker. Monitoring EKG activity during the magnetic mode indicates the condition of the pacemaker. The pacemaker may indicate battery condition, for example, by modifying the width of stimulation pulses generated by the pacemaker. In particular, when the battery goes low, stimulation pulse width increases. Pulse width data, therefore, is an important measurement taken during evaluation of a given pacemaker. Other pacemakers indicate a low battery condition by modification to the "magnetic" rate. When a battery low condition exists, the pacemaker "magnetic" rate may change, e.g., decreases by a given percentage.

A pacemaker monitor transmitter verifies that the pacemaker is programmed appropriately and that it can capture the heart, and determines the battery condition of the pacemaker. These tests can be performed in a physician's office, preferably every one to three months. Many physicians, especially in rural settings, do not want the patient to travel to the doctor's office to conduct these tests. Fortunately, these tests can be conducted remotely, i.e., via telephone connection between the pacemaker monitor transmitter and a receiving station at the doctor's office. This eliminates patient travel to the doctor's office.

Unfortunately, people with implanted pacemakers are usually elderly. These elderly patients, sometimes nervous and confused, must conduct pacemaker and heart monitoring sessions. Generally, the patient calls the doctor's office and performs certain actions in manipulation of the pacemaker monitor transmitter and pacemaker itself to stimulate the heartland pacemaker into appropriate modes for evaluation. Several steps are executed, and a person at the remote receiving station typically guides the patient through the session by voice instruction.

Early pacemaker monitor transmitters were chest-held units. Patients held the pacemaker monitor transmitter against their chest, held a telephone on the pacemaker monitor transmitter, held a magnet over the pacemaker, and remained as still as possible to minimize body motion artifact during transmission. If the patient does not remain still, body motion produces incorrect EKG data. More recent pacemaker monitor transmitter devices, however, comprise a self-contained box for all electrical components, a telephone cradle, and wires connected to electrodes contacting the patient. This more recent type of a pacemaker monitor transmitter reduces patient anxiety for its relatively more convenient use, but still exhibits certain problems.

A common problem with existing pacemaker monitor transmitter devices is difficulty in communicating with elderly patients. When problems occur, the receiving station must talk to the patient to instruct the patient step-by-step through the monitoring session. To obtain the patient's attention, a signal from the receiving center to the pacemaker monitor transmitter generates a tone at the telephone cradle or receiving unit. Unfortunately, such tones are for many patients difficult to hear. The tone delivered to the pacemaker monitor transmitter also activates a patient alert light on the device. When the patient sees this light, the patient picks up the telephone to interact verbally with the remote center. Some configurations require that a person at the remote station yell into the telephone with the hope that the patient hears the person yelling. Furthermore, verbal communication is hampered by the ongoing data transmission present on the telephone connection. The volume of the data transmission often overrides tone signals and voice communication on the telephone connection.

Another problem with existing pacemaker monitor transmitters is patient activity corrupting the EKG signal and rendering a reading useless. An EKG reading can in some cases be obtained in several seconds, whereas in other situations with excess motion artifact noise, the EKG readings may take 30 to 40 seconds. This indeterminacy furthers patient anxiety in not knowing when a given EKG reading is complete and when a new instruction need be received verbally from the remote station. In other words, often the patient does not know when a test step is complete and the person at the remote station cannot get the patient's attention.

Finally, data transmitted to the receiving station may take a variety of formats. Many receiving center stations collect data according to several data formats. Preferably, however, the receiving station need not be adjusted to match an incoming stream of data from a pacemaker monitor transmitter.

Accordingly, it is desirable to improve operation of a pacemaker monitor transmitter by reducing or eliminating patient anxiety and making more simple the process of conducting heart and pacemaker evaluation sessions. To the extent that patient anxiety and motion artifact can be minimized, an acceptable EKG reading may be taken more efficiently and thereby support the goal of monitoring at a remote station the condition of the patient's heart and pacemaker.

SUMMARY OF THE INVENTION

A pacemaker monitor transmitter device in accordance with a preferred form of the present invention couples to a patient having a pacemaker and interacts with a remote station including a remote operator. The pacemaker monitor transmitter device of the present invention includes a telephonic communication channel delivering a pacemaker monitor transmitter device generated signal and a patient voice signal into a telephone connection and receives from the telephone connection a remote signal including a command signal and remote operator voice signal. An electrode pair attaches to the patient and provides a patient signal to the device. A patient signal processing element receives the patient signal in analog form, converts the patient signal to digital form, and provides the patient signal to the telephonic channel in frequency modulated form as said device generated signal. The telephonic communication channel may include a cradle receiving a patient telephone handset, a hands-free microphone and speaker, and direct coupling to a telephone line jack. By converting the patient signal to digital form, the device of the present invention advantageously provides to the remote station the patient signal infrequency modulated form as digitally generated tones. The present invention contemplates use of a microcontroller to apply digital signal processing to the patient signal, including, for example, a finite impulse response filter function. The present invention further contemplates response by the device to commands generated at the remote station, including such commands as speaker volume increase, speaker volume decrease, toggle pulse width information in the patient signal, patient alert, and toggle a hands-free mode of operation.

In accordance with the present invention, a pacemaker monitor transmitter of the present invention includes a microcontroller, a telephonic communication channel coupled to the microcontroller whereby the device applies signals to a telephone connection and receives signals from the telephone connection, a patient signal interface including an electrode pair producing an analog patient signal and delivering the patient signal to the microcontroller whereby the microcontroller converts the patient signal to digital form, applies digital signal processing to the patient signal, and delivers the patient signal to the telephonic communication signal as digitally generated tones. Finally, the pacemaker monitor transmitter includes a command signal interface coupling the microcontroller to the telephonic communication channel whereby the microcontroller responds to signals received from the telephonic communication signal, e.g., such signals as originating from a remote station as produced by a remote station operator in implementation of a pacemaker monitor session.

The subject matter of the present invention is particularly pointed out and distinctly claimed in the concluding portion of this specification. However, both the organization and method of operation of the invention, together with further advantages and objects thereof, may best be understood by reference to the following description taken with the accompanying drawings wherein like reference characters refer to like elements.

BRIEF DESCRIPTION OF THE DRAWINGS

For a better understanding of the invention, and to show how the same may be carried into effect, reference will now be made, by way of example, to the accompanying drawings in which.

DETAILED DESCRIPTION OF THE PREFERRED EMBODIMENT

Figure 1:
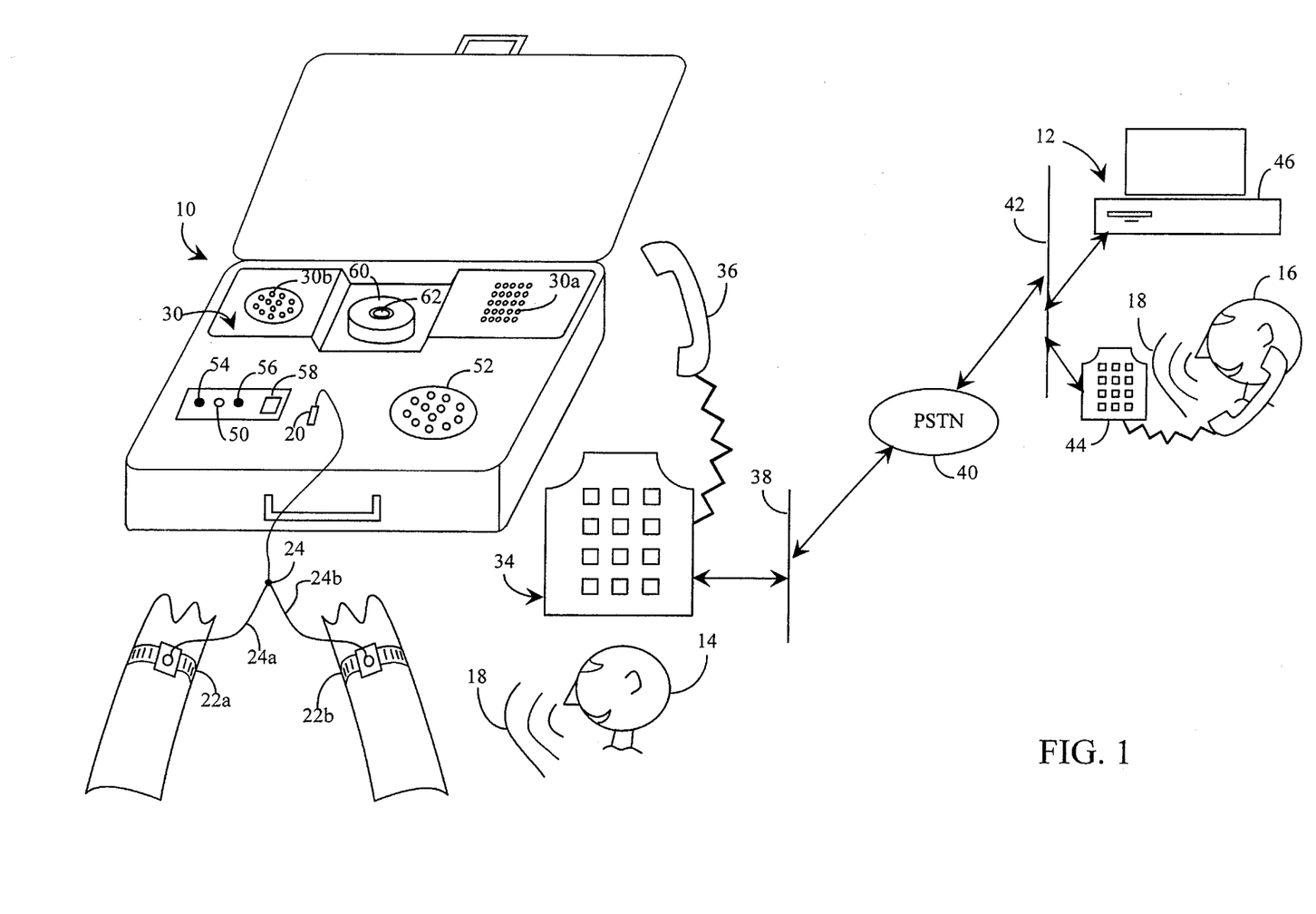
FIG. 1 illustrates a pacemaker monitor according to a preferred embodiment of the present invention and its relationship to telephone and remote monitoring station equipment in use thereof.

FIG. 1 illustrates a pacemaker monitor transmitter 10 coupled via telephone connection to a remote receiving station 12. A patient 14 interacts with a data recipient 16 operating remote station 12 to conduct a pacemaker and heart monitoring session using pacemaker monitor transmitter 10. Pacemaker monitor device 10 interacts electronically with the remote receiving station 12. Further, patient 14 must interact verbally, as indicated by reference numeral 18 in FIG. 1, with the recipient 16.

Pacemaker monitor transmitter 10 includes an electrode jack 20 coupled to an electrode pair 22, individually wrist band electrodes 22a and 22b, by way of electrode conductors 24, individually 24a and 24b. As may be appreciated, however, an electrode pair may also be applied to the patient 14 fingertips or to chest locations via chest pads. Pacemaker monitor 10 thereby receives from patient 14 an EKG signal for processing and transmission to receiving device 12.

Pacemaker monitor transmitter 10 provides a phone cradle 30, including a cradle speaker 30a and a cradle microphone 30b. A patient telephone 34 includes a handset 36. Telephone 34 operates on patient telephone line 38 connected by public switch telephone network (PSTN) 40 to a recipient's telephone line 42. A recipient telephone 44 and a data receiving device 46 operate on recipient's telephone line 42. In this manner, placing handset 36 of telephone 34 on cradle 30 allows pacemaker monitor transmitter 10 to interact with data receiving device 46 by way of telephone connection. Patient 14 also holds handset 36 to his or her mouth and ear to interact verbally, as indicated at reference numeral 18 in FIG. 1, with the recipient 16 using recipient's telephone 44.

Pacemaker monitor transmitter 10 also operates in a "hands-free" mode whereby patient 14 interacts verbally with recipient 16 without removing handset 36 from cradle 30. This improves the convenience of use for patient 14. Thus, pacemaker monitor transmitter 10 includes a hands-free microphone 50 and a hands-free speaker 52 allowing patient 14 to interact via telephone connection with the recipient 16 in a "hands-free" mode.

Pacemaker monitor 10 includes a "patient alert" or "pick-up phone" indicator 54 selectably activated from station 12 to indicate to patient 14 need to interact verbally, e.g., pick up handset 36 from cradle 30 and interact verbally with recipient 16. Furthermore, recipient 16 may toggle pacemaker monitor transmitter 10 into and out of the "hands-free" mode whereby recipient 16 may initiate "hands-free" mode and speak directly to the patient 14 via microphone 50 and speaker 52 of pacemaker monitor 10. Pacemaker monitor transmitter 10 includes a low battery indicator 56, and a power switch 58 illuminated when in its "on" position.

An annular magnet 60 rests on a post 62 of pacemaker monitor transmitter 10. When appropriate, patient 14 removes magnet 60 from post 62 and holds magnet 60 over the implanted pacemaker. This triggers the pacemaker into "magnetic" mode to support evaluation of pacemaker operation.

Remote receiving station 12 receives an EKG signal taken from patient 14 via electrodes 22. Also, station 12 receives information concerning the battery condition of the pacemaker implanted in patient 14. By regularly monitoring patient 14 heart and pacemaker conditions, receiving station 12 ensures ongoing and stable condition for patient 14 and its implanted pacemaker. This avoids patient 14 travelling to a doctor's office for routine monitoring of the pacemaker and heart condition.

Figure 2:
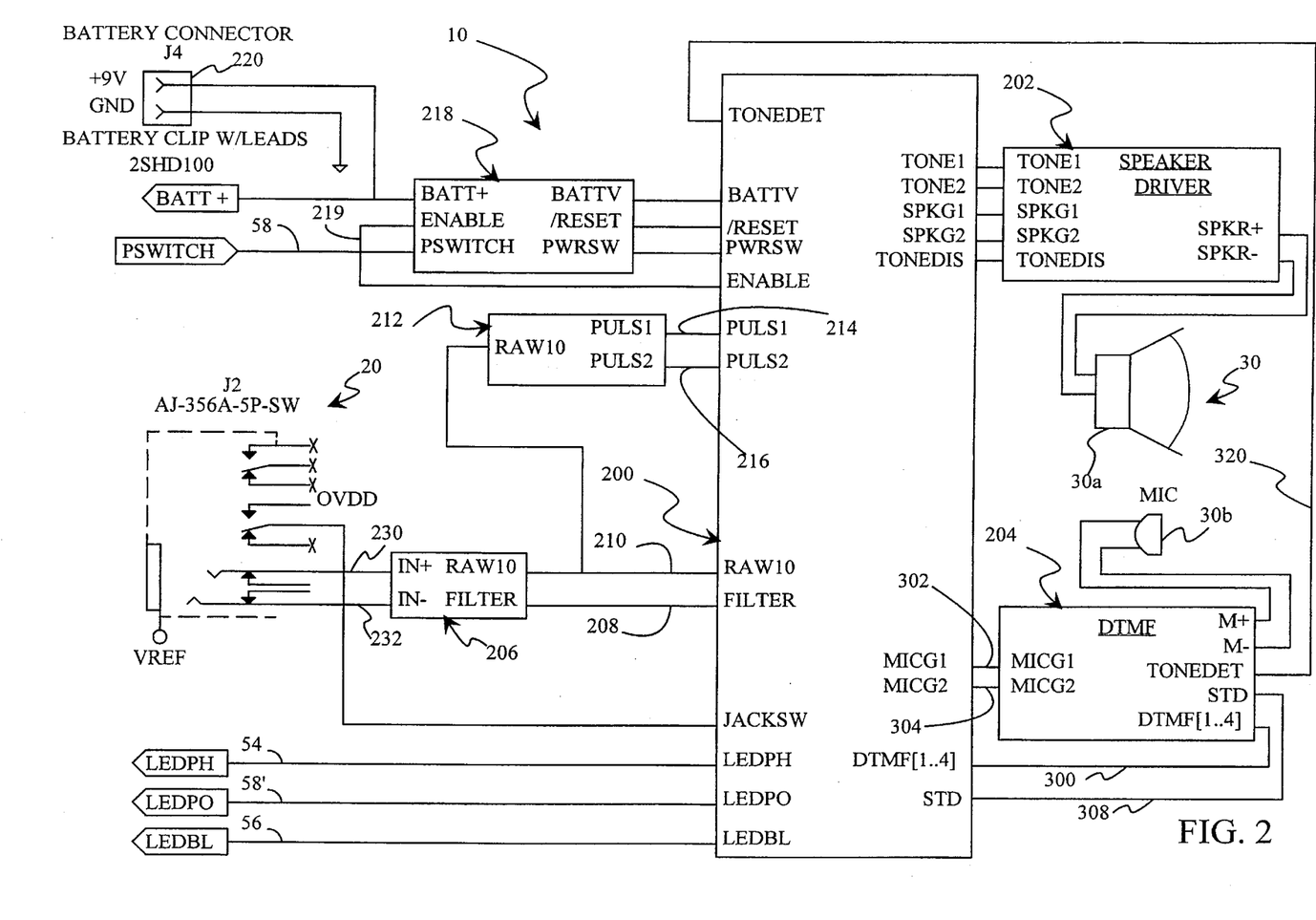
FIG. 2 illustrates by block diagram the electrical circuitry of the pacemaker monitor transmitter of FIG. 1.

FIG. 2 illustrates in block diagram circuitry for the pacemaker monitor transmitter 10. In FIG. 2, a microcontroller 200 orchestrates generally operation of pacemaker monitor transmitter 10 according to programmed control. While a variety of specific microcontroller products suitably support operation of pacemaker monitor transmitter 10, the particular embodiment illustrated herein uses a microcontroller available under product number MC68HC711E9CFN2.

Microcontroller 200 drives LED indicators 54 and 56 of device 10 as well as the illuminated LED portion 58' of power switch 58.

A speaker driver block 202 interposed between microcontroller 200 and cradle speaker 30a injects sound into the handset 36 of patient telephone 34, i.e., delivers EKG and pulse width information to remote receiving station 12 via telephone connection. A DTMF receiver/decoder block 204 interposed between microcontroller 200 and cradle microphone 30b collects information, i.e., collects commands at handset 36 originating from remote station 12 as DTMF codes.

An EKG amplifier block 206 interposed between electrode jack 20 and microcontroller 200 delivers to microcontroller 200 a filtered EKG signal 208 and an amplified raw EKG signal 210. A pulse discriminator block 212 also receives the amplified raw EKG signal 210 and provides to microcontroller 200 pulse signals 214 and 216. Signals 208 and 210 vary in voltage as representation of the electrical heart activity detected by electrodes 22. Microcontroller 200 performs digital signal processing (DSP) relative to signals 208 and 210 and drives onto cradle 30 at speaker 30a frequency modulated tone signals representative thereof to deliver EKG waveform information to remote station 12. Further, pulse discriminator block 212 provides, via pulse signals 214 and 216, indication to microcontroller 200 of the onset and conclusion of stimulation pulses produced by an implanted pacemaker device. By measuring a time interval between occurrence of pulse signals 214 and 216, microcontroller 200 measures the pulse width of a pacemaker stimulation pulse.

A power supply block 218 couples to a battery connector 220 to provide power to pacemaker monitor transmitter 10. Power switch 58 couples to power supply block 218 and dictates application of power. Pressing power switch 58 applies power, which in turn causes microcontroller 200 to begin executing its programming. Microcontroller 200 sustains the power via an enable signal 219 applied to power supply block 218. In this manner, pacemaker monitor transmitter 10 operation continues once the operator disengages, i.e., removes his or her finger, from power switch 58.

Figure 3:
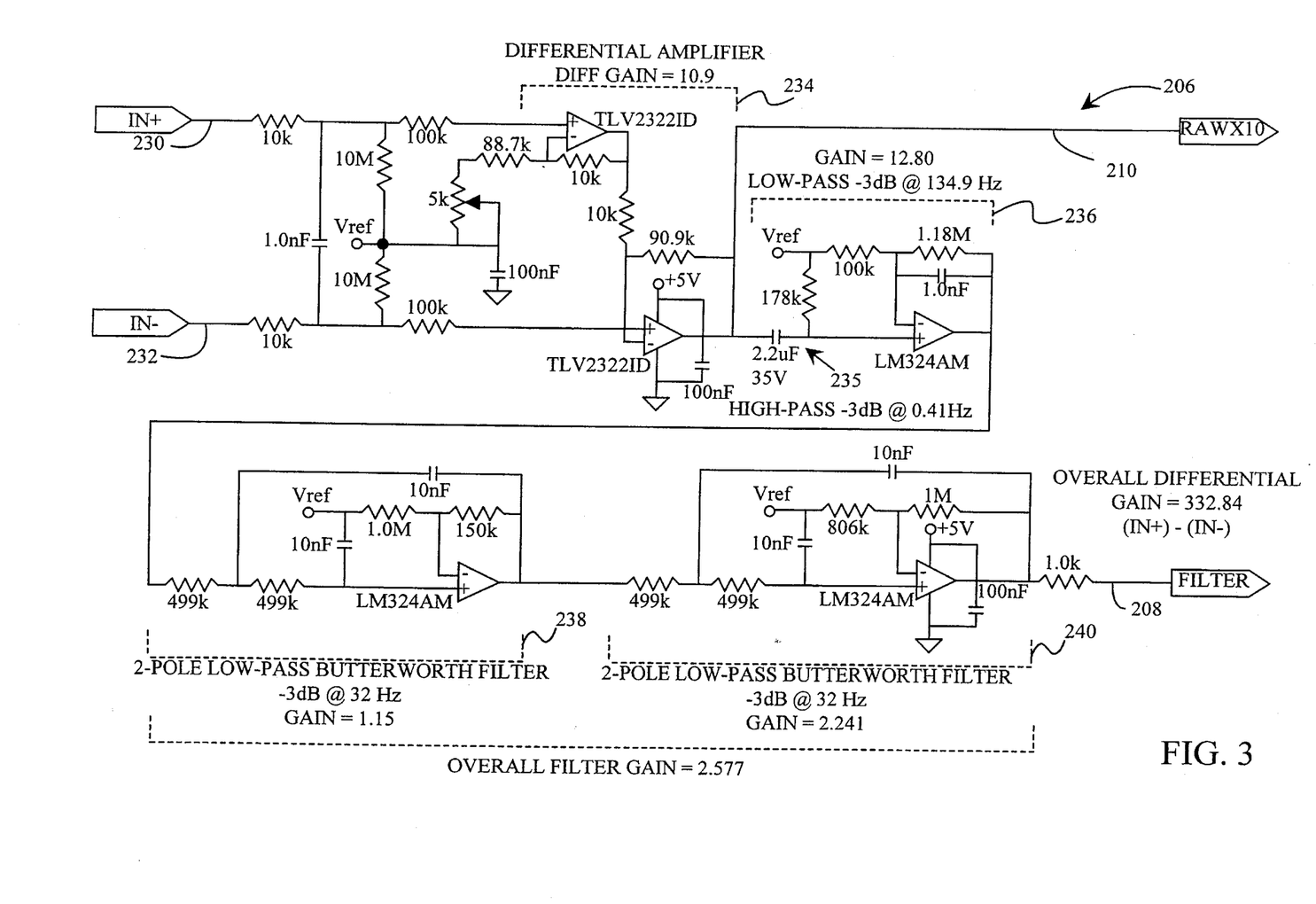
FIG. 3 illustrates an EKG amplifier of the pacemaker monitor transmitter of the present invention.

FIG. 3 illustrates by schematic diagram the EKG amplifier block 206. With reference to FIG. 3 in conjunction with FIG. 2, EKG amplifier 206 includes a series of amplification stages to produce the amplified raw EKG signal 210, and by subsequent filtering stages, the filtered EKG signal 208. Electrode inputs 230 and 232 couple, via jack 20, to electrodes 22 (FIG. 1). A differential amplifier 234 produces the amplified EKG signal 210, and includes input circuitry filtering undesirable interference, e.g., RF frequencies, potentially collected by electrodes 22. Subsequent to differential amplifier 234, a series of low pass filters 236, 238, and 240 develop the filtered EKG signal 208. Of note, output signals 208 and 210 provided by block 206 are generally varying DC voltages, but are AC coupled to 0.5 Hz subsequent to the differential amplifier 234. In this manner, pulse discriminator 212 is AC coupled, by virtue of capacitor 211 (FIG. 4A) blocking all DC components of the signal 210. Pacemaker pulses tend to have fast rise and fall times, and therefore a significant high-frequency content. Accordingly, the signal 210 applied to pulse discriminator circuit 212 is not low-pass filtered in such manner as to negatively impact pulse detection. A highpass filter 235, appearing just subsequent to differential amplifier 234, blocks any DC potential at the patient's wrist which would overload the subsequent amplifier stages.

Figures 4A, 4B:
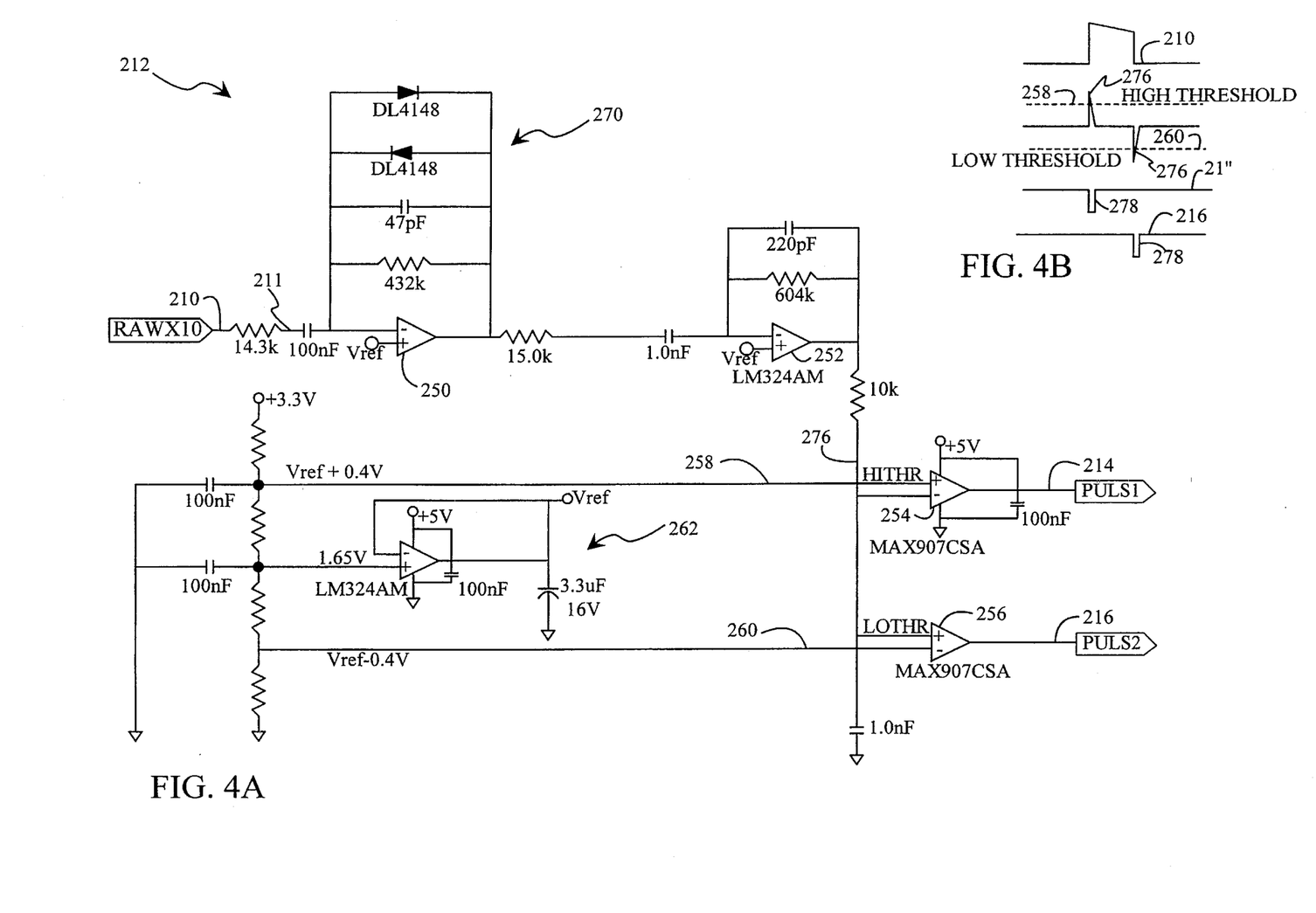
FIGS. 4A and 4B illustrate a pulse discriminator circuit and signal waveforms of the pacemaker monitor transmitter of the present invention.

FIGS. 4A and 4B illustrate by schematic diagram and by signal waveform, respectively, the pulse discriminator circuit 212 of FIG. 2. With reference to FIGS. 4A and 4B in conjunction with FIG. 2, pulse discriminator circuit 212 receives the amplified, in this case a ten-fold gain, EKG signal 210 and generates the pulse signals 214 and 216 for application to microcontroller 200. Pulse signals 214 and 216 trigger interrupt programming (FIG. 9) of microcontroller 200 responsible for measuring a time interval between occurrence of pulse signals 214 and 216.

Pulse signals 214 and 216 represent edge events in a detected stimulation signal produced by an implanted pacemaker. Either one of signals 214 or 216 can represent the leading edge of a given stimulation pulse, with the other one of signals 214 and 216 representing the trailing edge of the given stimulation pulse. Thus, depending on the polarity of the stimulation pulse as presented in signal 210, positioning of electrodes 22 on patient 14, and the particular pacemaker generating the stimulation pulse, one of signals 214 and 216 will represent a leading edge of a stimulation pulse.

Figure 9:
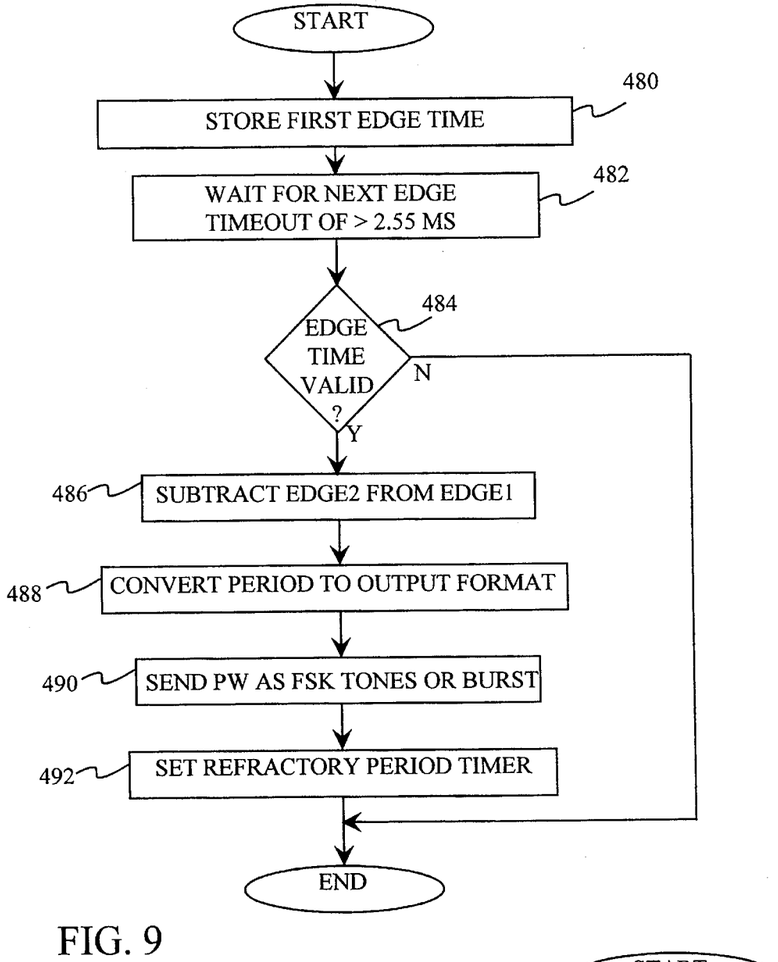
FIG. 9 is a control flow diagram illustrating an interrupt procedure measuring pulse width for a pacemaker stimulation pulse and reporting measured pulse width to a remote receiving station.

Occurrence of one of signals 214 and 216 triggers the interrupt procedure of FIG. 9 in microcontroller 200 whereby the other one of signals 214 and 216 is monitored to measure a time interval representing pulse width of the pacemaker stimulation pulse. The trailing edge of a valid stimulation pulse must occur within a given time window and the interrupt procedure validates the stimulation pulse relative to the required pulse width or window of valid occurrence.

Referring specifically now to FIGS. 4A and 4B, OPAMPS 250 and 252 along with corresponding feedback and coupling components establish differentiation circuitry for application to the comparators 254 and 256. Diode clamping circuitry 270 ensures the input signal 210 as presented to subsequent circuitry is within a given predictable amplitude range. Comparator 254 drives pulse signal 214 and comparator 256 drives pulse signal 216. Each of comparators 254 and 256 receive corresponding high threshold and low threshold voltage reference signals 258 and 260. Voltage reference circuitry 262 provides the threshold reference levels 258 and 260.

A pacemaker stimulation signal 210 is a generally square waveform with sharp rise and fall times producing significant high frequency components. In contrast, electrical heart activity follows a much smoother contoured waveform. Differentiation circuitry of discriminator 212 detects the sharp rise and fall times for edge events in signal 210 associated with onset and conclusion of a pacemaker stimulation pulse. In response to such high frequency component signals, OPAMP 252 presents positive and negative spike signals 276 (FIG. 4B) coincident with stimulation pulse edge events in signal 210. OPAMPS 254 and 256 respond to spikes 276 by producing pulses 278 in each of signals 214 and 216. As indicated herein above, one of signals 214 and 216 produces a first pulse 278 with the second pulse 278 appearing in the other one of signals 214 and 216. Microcontroller 200 measures an interval of time between pulses 278, i.e., measure the pulse width of a signal 210 pacemaker stimulation pulse.

Figure 5:
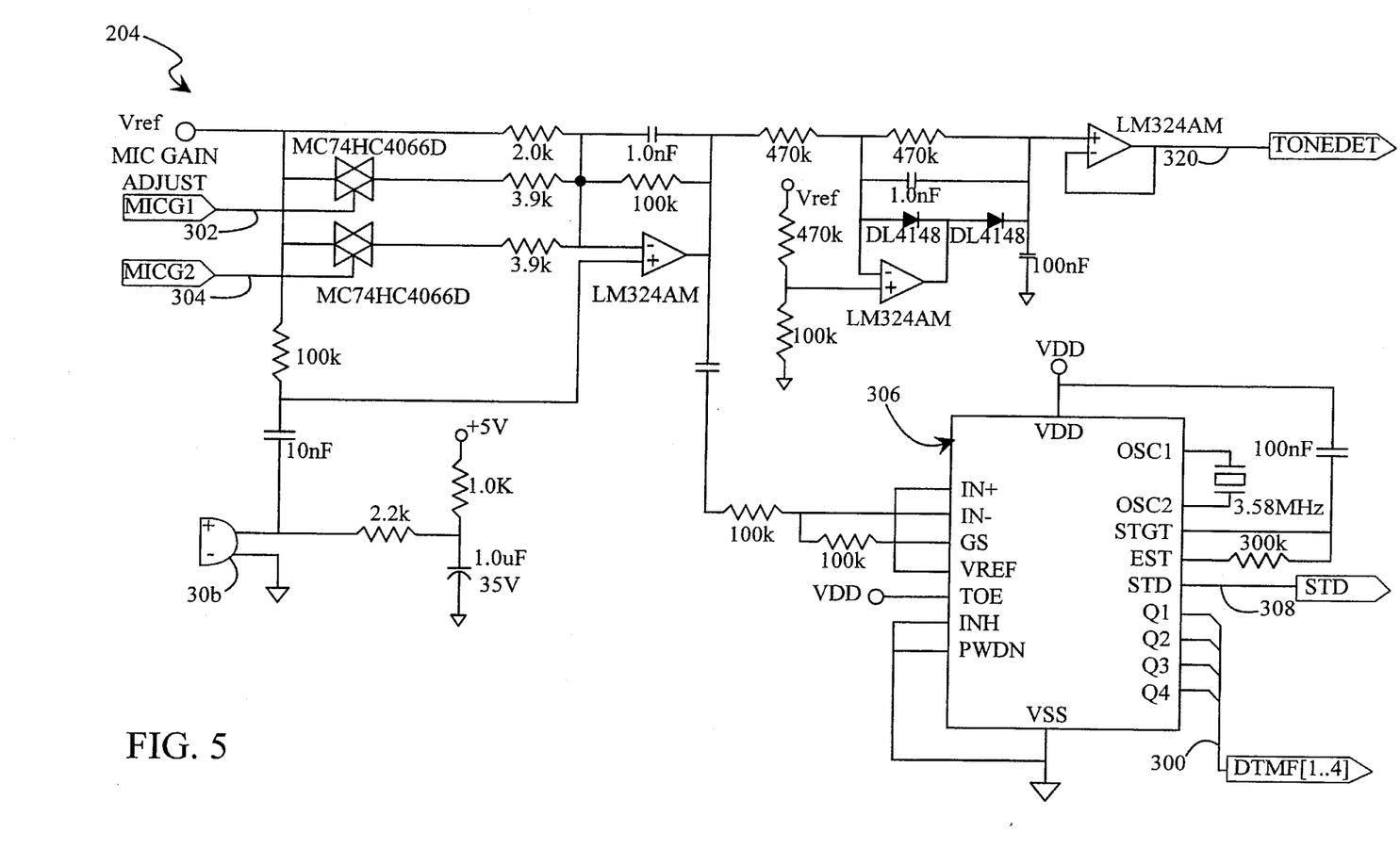
FIG. 5 illustrates a DTMF receiver/decoder of the pacemaker monitor transmitter of the present invention.

FIG. 5 illustrates by schematic diagram the DTMF receiver/decoder block 204 of FIG. 1. With reference to FIG. 2 in conjunction with FIG. 5, block 204 collects DTMF tones and generates a DTMF code word 300 for application to microcontroller 200. DTMF code word 300 is a four bit word representing a detected DTMF signal, i.e., as generated by recipient 16 on recipient's telephone 44 keypad. Recipient 16 thereby remotely drives or commands pacemaker monitor transmitter 10.

Microcontroller 200 manipulates DTMF receiver/decoder block 204 with microphone gain adjust signals 302 and 304. Signals 302 and 304 provide gain control relative to incoming telephone signals, e.g., as taken at microphone 30b. Because patient telephones 34 vary significantly with no control over the type of telephone used by patient 14, microphone gain adjust signals 302 and 304 advantageously provide adjustment in the signal taken from microphone 30b to accommodate variations in a patient 14 telephone 34. Pacemaker monitor transmitter 10 thereby accommodates particular acoustic features of telephone 34 and its handset 36 placement in cradle 30.

Receiver/decoder block 204 is implemented by use of a DTMF decoder circuit 306 available from Mitel Semiconductor under product number MT88L70AS. Circuit 306 produces a signal tone detected (STD) signal 308 indicating collection of a valid DTMF signal. Microcontroller 200 intermittently polls STD signal 308 and, when appropriate, collects a DTMF codeword 300 from circuit 306. Microcontroller 200 should poll the signal 308 frequently to avoid loss of information, i.e., a subsequent DTMF code overriding a previous DTMF codeword 300 not yet collected by microcontroller 200.

Block 204 also provides to microcontroller 200 a tone detect signal 320. Generally, tone detect signal 320 is an energy magnitude detector, i.e., an analog signal representing the energy envelope of any received tone. Signal 320 presents to microcontroller 200 a voltage corresponding to the amplitude of any tone present at microphone 30b. This allows device 10 to determine how well the microphone 30b is picking up information from the patient telephone handset 36. As feedback to microcontroller 200, signal 320 provides a basis for adjustment in the microphone 30b gain adjust signals 302 and 304. Thus, if the speaker 30a is particularly well coupled to the microphone 30b by way of patient handset 36, microcontroller 200 detects excess energy via tone detect signal 320 and reduces gain adjust signals 302 and 304. This avoids device 10 detecting at microphone 30b its own EKG transmission at speaker 30a. Microcontroller 200 thereby balances the transmitted signal amplitude at speaker 30a with the microphone 30b gain in relation to the patient telephone 34 coupling to cradle 30 to avoid masking of DTMF signals originating from remote station 12.

Figure 6:
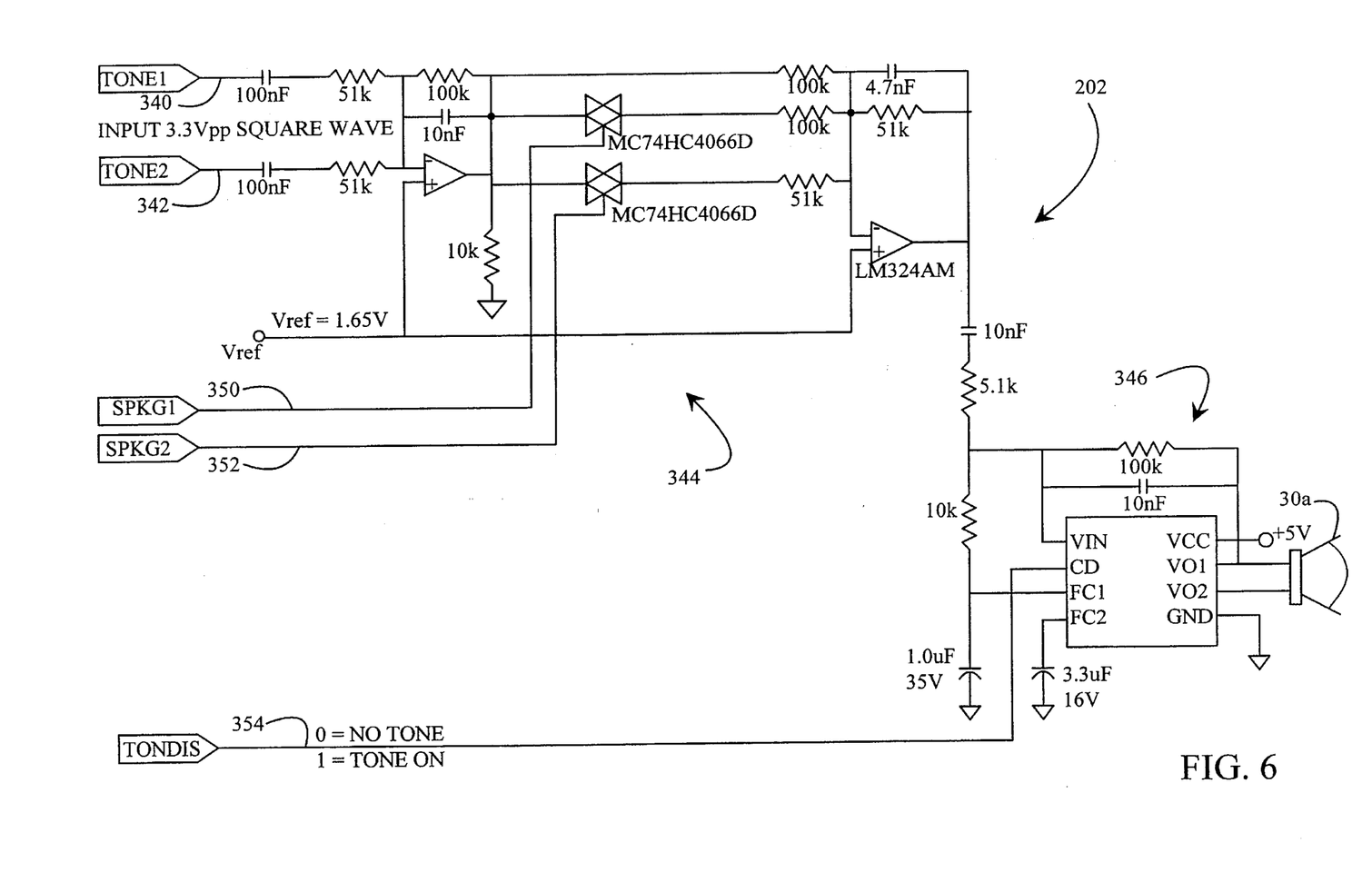
FIG. 6 illustrates a speaker driver of the pacemaker monitor transmitter of the present invention.

FIG. 6 illustrates by schematic diagram the speaker driver block 202. With reference to FIG. 6 in conjunction with FIG. 2, speaker driver block 202 receives from microcontroller 200 tone signals 340 and 342. Each of tone signals 340 and 342 is a square wave signal with 50 percent duty cycle originating from microcontroller 200. The square wave signals 340 and 342, as collected from microcontroller 200, are rich in harmonics due to the sharp rise and fall times therein. The data receiving device 46 at remote station 12 may not appropriately reject such harmonics. It is desirable, therefore, to remove frequency harmonics from any signal delivered to data receiving device 46. Generally, this is accomplished by integrating the square wave from signals 340 and 342 to produce a triangle wave. This causes, however, the amplitude of the triangle wave to be inversely proportional to the frequency. Thus, as frequency increases, the amplitude of the output decreases. Ordinarily, this relationship would be undesirable, but experimentation has shown that the overall frequency response of the plastic enclosure and speaker of pacemaker monitor transmitter 10 and the associated telephone connection tend to compensate for this loss in output amplitude as a function of an increase in frequency. Accordingly, the overall result is a fairly flat frequency response as delivered to the remote station 12.

Only tone signal 340 is used to drive an EKG signal onto speaker 30a. In normal operation, tone signal 340 represents, in the frequency thereof, an EKG signal as detected by electrodes 22 and digitally processed within microcontroller 200. Circuitry 344 filters and converts the square wave originating in signals 340 and 342 into a generally triangular wave. With relatively lower harmonic content, i.e., slower rise and fall times. The triangular waveform is further filtered by the feedback network 346 as coupled to the speaker driver device 348 as available under product number MC34119D. As a result, the signal applied to speaker 30a is virtually a sine wave, having little high frequency component. Block 202 also receives speaker gain signals 350 and 352 for balancing signals driven onto telephone handset 36 by way of speaker 30a in relation to information taken from handset 36 by way of microphone 30b.

Signals 340 and 342 can be used concurrently i.e., to produce two frequencies according to DTMF protocol. For example, such feature may be employed to facilitate automatic dialing by device 10.

Speaker driver block 202 also receives from microcontroller 200 a tone disable signal 354. Tone disable signal 354 applies to speaker driver device 348 to shut down operation thereof when desired, e.g., stop EKG signal transmission when verbal interaction is required between patient 14 and recipient 16.

Figure 7:
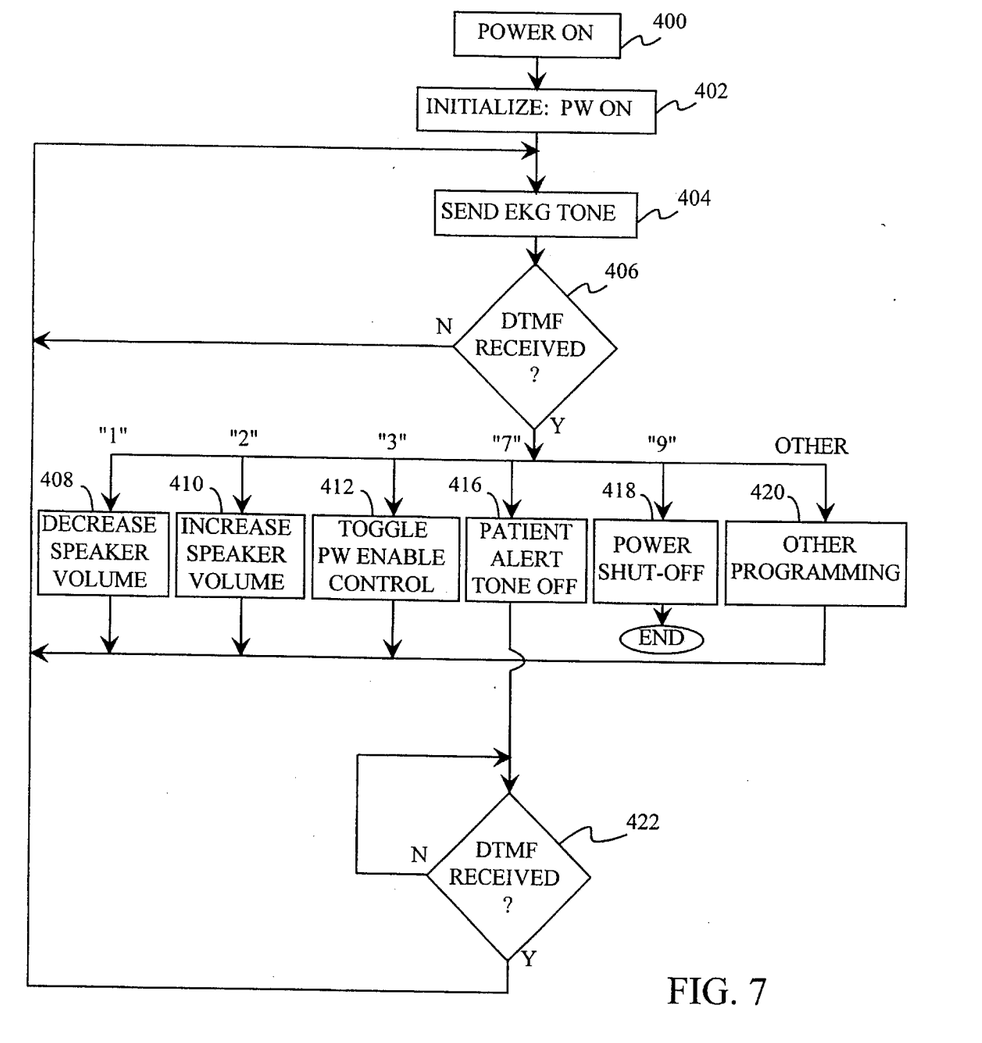
FIG. 7 is an overall control flow diagram for microcontroller programming of the pacemaker monitor transmitter of the present invention.

FIG. 7 illustrates generally overall control flow programming for microcontroller 200. In FIG. 7, processing begins in block 400 where pacemaker monitor transmitter 10 responds to activation of power switch 58 (FIG. 2). As noted above, power supply block 218 provides power to microcontroller 200 in response to activation of switch 58. In block 402, microcontroller 200 sustains the power supply by way of enable signal 219 and initializes certain variables and configuration registers in implementation of subsequent programming.

Figure 8:
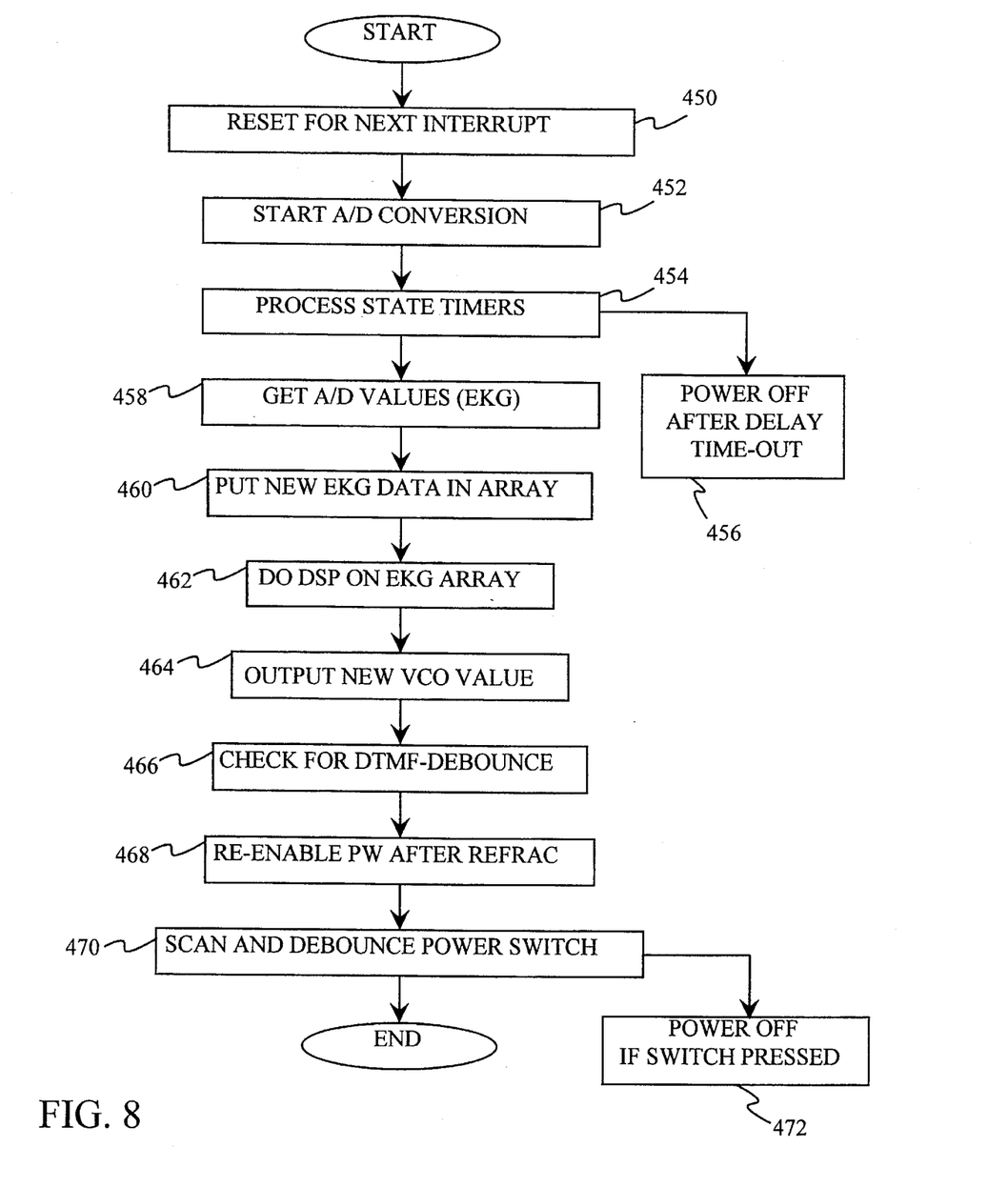
FIG. 8 is a flow diagram illustrating a background interrupt process executed by the microcontroller of the present invention and responsible generally for collecting EKG data, processing EKG data, and broadcasting EKG data to a remote receiving station.
Figure 10:
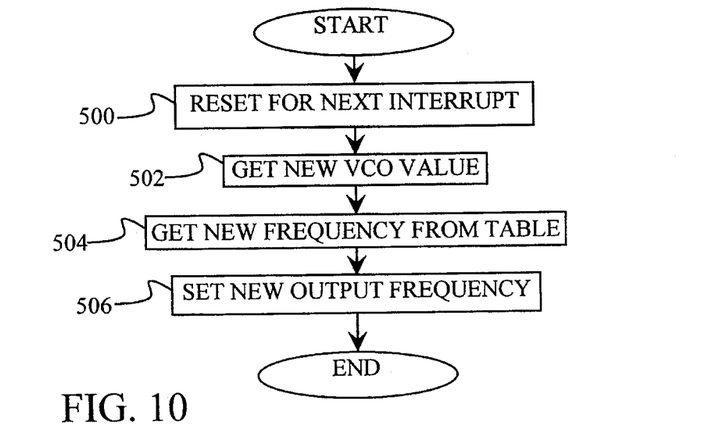
FIG. 10 is an interrupt procedure executed by the microcontroller of the present invention and provided in implementation of a firmware voltage controlled oscillator.

Block 404 of the main programming control flow represents opportunity for microcontroller 200 to execute a variety of interrupt and timer initiated programming as described hereafter with reference to FIGS. 8–10. Generally, block 404 represents an interruptable foreground program wherein microcontroller 200 otherwise waits for a DTMF command received from the remote station 12. Thus, microcontroller 200 is intermittently interrupted and processes programming represented in FIG. 8. While microcontroller 200 is executing programming of FIG. 8 or while executing the mainline programming of FIG. 9, additional interrupt procedures can trigger processing illustrated in FIGS. 9 and 10. Following block 404, decision block 406 determines whether a valid DTMF tone has been received. As described more fully hereafter, a DTMF tone is considered valid when present for a given period of time as detected by steps executed in FIG. 8 and represented by a corresponding flag variable representing valid DTMF tone received. If no valid DTMF tone has been received, processing simply loops through to block 404.

When a valid DTMF tone has been received, however, processing advances to a switch structure responsive to specific DTMF tones. In this manner, the recipient 16 at remote station 12 drives or controls operation of pacemaker monitor transmitter 10. Pressing a "1" on the keypad of recipient telephone 44 causes microcontroller 200 to decrease speaker volume in block 408, pressing a "2" causes microcontroller to increase speaker volume in block 410, pressing a "3" toggles a pulse width enable control flag which determines whether or not pacemaker stimulation pulse width data is transmitted to remote station 12, pressing a "7" initiates a patient alert mode in block 416, pressing a "9" causes microcontroller 200 to execute a power shut-off mode in block 418, and pressing any other DTMF code allows microcontroller 200 to execute other programming as represented by block 420. The programming represented in block 420 may take a variety of forms, corresponding to other features which may be desired in implementation of the present invention and not illustrated in blocks 408, 410, 412, 416, and 418.

Returning to the patient alert block 416, microcontroller 200 sets off an alarm audible to patient 14 and also begins flashing LED indicator 54. Microcontroller 200 also disables all other activity during execution of block 416, i.e., stops sending EKG and pulse width information to remote station 12, essentially placing pacemaker monitor transmitter 10 in a suspended mode. During such suspended mode, the patient 14 and recipient 16 may interact verbally allowing the recipient 16 to instruct patient 14 as to a next step in the monitoring session. While such verbal interaction occurs, microcontroller 200 loops at decision block 422 until a valid DTMF tone has been received. Once a valid DTMF tone is received, processing returns to block 404 wherein microcontroller 200 resumes normal activity, i.e., sending EKG information.

Thus, pacemaker monitor transmitter 10 allows remote control by means of DTMF tones originating from the remote station 12. As may be appreciated, a variety of functions beyond that shown herein may be implemented by additional branch paths provided in the switch structure of FIG. 7.

FIG. 8 represents a timed interrupt routine executed, in the illustrated embodiment, at a rate of 960 hz to provide opportunity for microcontroller 200 to collect EKG data, monitor and set certain state variables, debounce switch activity, and validate DTMF tone conditions. In FIG. 8, processing begins in block 450 where microcontroller 200 resets a timer for the next occurrence of FIG. 8 programming in implementation of a given interrupt rate, i.e., to establish a 960 hz rate of execution. Block 452 represents collection of analog voltage EKG values and initiation of analog to digital (A/D) conversion. Continuing to block 454, microcontroller 200 processes a variety of state timers. For example, microcontroller 200 may be programmed to automatically cease operation if no activity has occurred for a given period of time, i.e., a time-out condition for automatic power off as represented in the branch from block 454 to block 456 executing a power off after delayed time-out. Continuing to block 458, microcontroller 200 collects the result of A/D conversion and establishes in block 460 new entries in an EKG data array.

Continuing to block 462, microcontroller 200 executes when necessary digital signal processing (DSP) on the EKG data array. Thus, a reading is taken intermittently from the electrodes 22 and a corresponding digital value placed in an EKG data array. When first initialized, the data array has null values, but is eventually filled with a digital representation of EKG voltage values taken from electrodes 22. This array is filled on a first-in-first-out (FIFO) basis. Once filled, every time a new value is placed in the EKG data array, a DSP algorithm is executed. In the preferred embodiment of the present invention, a finite impulse response (FIR) filter algorithm performs a mathematical operation on every element of the EKG data array. Because the EKG data is provided under the present invention in digital form, microcontroller 200 advantageously performs digital signal processing before reporting such data to remote station 12. Generally, the finite impulse response algorithm multiplies each element in the EKG array by a corresponding coefficient in accordance with known digital signal processing methods. By then summing the resulting products an output value representing the current state of the EKG data array is obtained. This output value is then fed to a software voltage controlled oscillator (VCO) routine represented in FIG. 10. Block 464 represents delivery of the output provided by the DSP algorithm to the software VCO of FIG. 10. Generally, the output value is converted to a frequency value used to provide a square wave to the speaker driver 202 (FIG. 2) as described above. In particular, the frequency of such square wave corresponds to a representation of voltage at a given time in the EKG signal taken from electrodes 22. Thus, the instantaneous frequency determined by the output of the DSP finite impulse response algorithm is proportional to the measured EKG voltage taken from electrodes 22. As discussed above, the resulting square wave has a corresponding frequency as applied to speaker driver 202 and is thereby reported to remote station 12. In this manner, EKG data is frequency modulated as applied over the telephone connection with remote station 12, and remote station 12 then converts the frequency modulated EKG data into a "strip", i.e., a printout or display, representing heart activity of patient 14.

In block 466, microcontroller 200 checks for DTMF debounce. More particularly, block 466 monitors a detected DTMF tone as provided by DTMF block 204 (FIG. 2) and, if such tone is present for sufficient time, sets a flag indicating receipt of a valid DTMF tone. As noted above with reference to FIG. 7, decision blocks 406 and 422 reference this flag to validate receipt of a DTMF tone from remote station 12.

In block 468, microcontroller 200 references a refractory period to enable, when appropriate, detection of pacemaker stimulation pulses. Because pacemaker stimulation pulses occur at regular intervals, microcontroller 200 disables detection of pacemaker stimulation pulses at other times. This allows microcontroller 200 to ignore noise conditions which may possibly be inaccurately reported as pacemaker stimulation pulses. Thus, programming in block 468 represents enabling of pacemaker stimulation pulse detection at an appropriate time.

In block 470, microcontroller 200 scans the condition of power switch 58, and if a change in state, i.e., a power-off condition, has endured for sufficient period of time then processing branches to block 472 where microcontroller deactivates power supply 218, i.e., turns itself off. Otherwise, processing exits the interrupt routine from block 470.

FIG. 9 illustrates an interrupt routine responsive to presentation of an edge event in the pacemaker stimulation pulse. As described herein above, signals 214 and 216 represent edge events in a pacemaker stimulation pulse as detected by block 212 (FIG. 2). Programming represented in FIG. 9 is initiated in response to either one of signals 214 or 216. In block 480, microcontroller 200 stores a time stamp associated with the first one of signals 214 and 216. Continuing to block 482, microcontroller 200 waits for the next occurrence of one of signals 214 and 216 and upon such occurrence stores a time stamp associated therewith. If the difference between the first and second time stamps occurs outside a given pacemaker stimulation pulse validation window, then processing branches at decision block 484 to exit the routine of FIG. 9.

If, however, the difference between the first and second time stamps validates the width of the detected pacemaker stimulation pulse, then processing advances to block 468 where the width or period of the stimulation is calculated. Continuing to block 488, microcontroller 200 converts the period calculated in block 468 to an appropriate output format, e.g., a frequency shift key tone burst format. Then, in block 490, the output format is sent as pulse width information via the telephone connection in the form of frequency shift key (FSK) tones or bursts. As may be appreciated, remote station 12 responds to such FSK tones or bursts by noting the indicated stimulation pulse width.

With reference to FIG. 7, remote station 12 can deactivate reporting of pulse width information by pressing a "3". In such case, programming of block 490 (FIG. 9) does not send out the FSK tone or burst.

Continuing to block 492, microcontroller 200 sets a refractory period timer indicating a next expected occurrence of a pacemaker stimulation pulse. As may be appreciated, programming in block 468 of FIG. 8 references such refractory period timer to re-enable pacemaker stimulation pulse width monitoring and, if appropriate, reporting to remote station 12.

FIG. 10 is a timer interrupt program providing a software "voltage controlled oscillator" (VCO) as noted above. The result of the finite impulse response (FIR) algorithm against the EKG data array provides as output an instantaneous frequency reported to the programming of FIG. 10 by means of a VCO value established in block 464 of FIG. 8. In FIG. 10, processing begins in block 500 where microcontroller 200 resets an appropriate timer to reactivate a next occurrence of the programming of FIG. 10. In block 502, microcontroller 200 obtains the VCO value reported in block 464 of FIG. 8. Microcontroller 200 uses a look-up table in block 504 to convert the VCO value to an appropriate frequency value. This avoids calculation of such value by microcontroller 200 upon every execution of programming in FIG. 10. Continuing to block 506, microcontroller 200 sets the new output frequency, and thereby establishes the frequency of a square wave applied to speaker driver 202 and representing the EKG signal in frequency modulated form.

Figure 11:
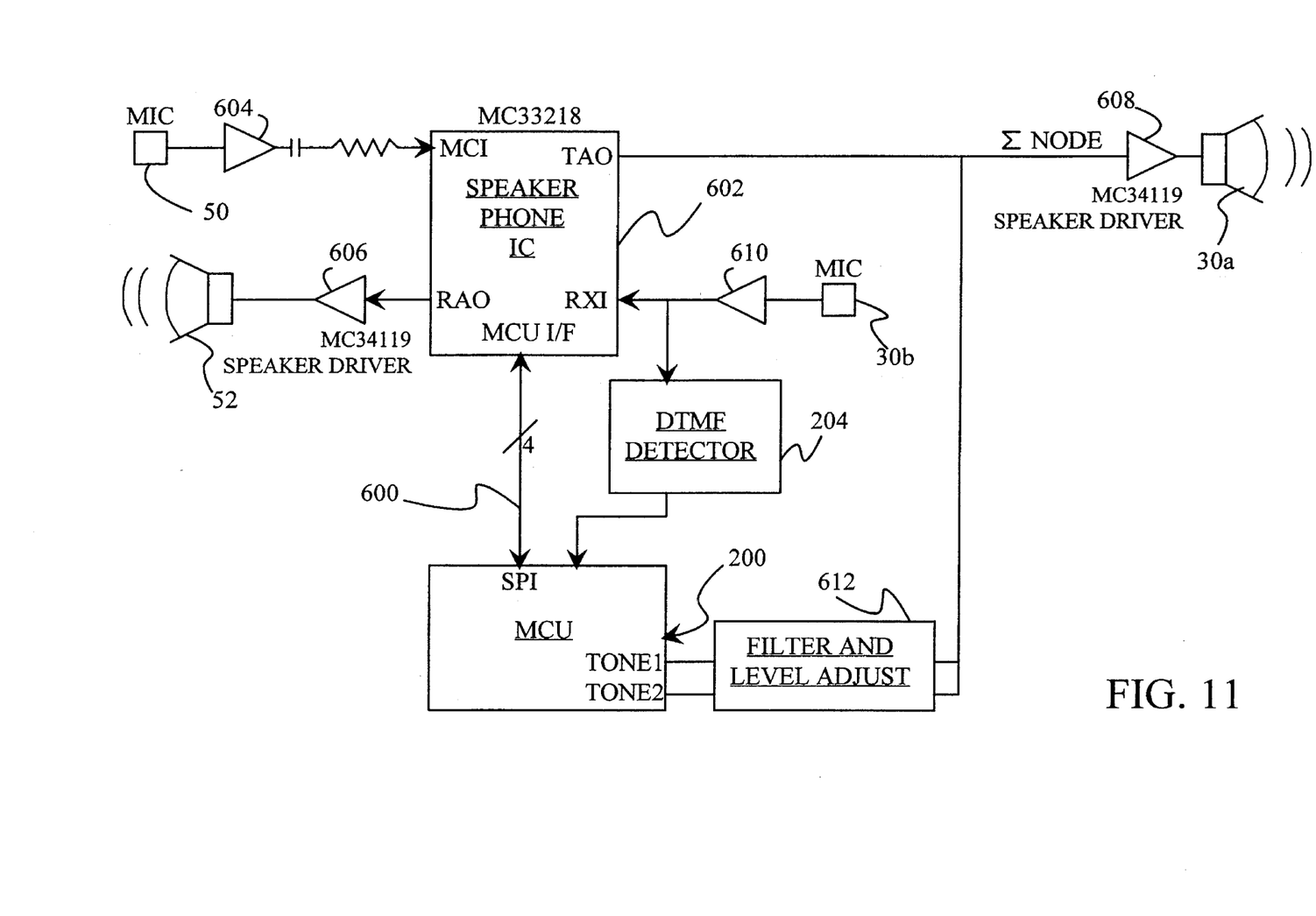
FIG. 11 is a simplified block diagram illustrating implementation of a hands-free embodiment of the present invention.

FIG. 11 illustrates in abbreviated form incorporation of the hands-free feature of the present invention. FIG. 11 corresponds generally to FIG. 2, but omits circuitry not relevant to the hands-free mode of operation. In FIG. 11, microcontroller 200 interacts by way of a serial bus 600 with a speaker phone integrated circuit (IC) provided, in the illustrated embodiment, by product number MC33218 and indicated in FIG. 11 as the speaker phone IC 602. Speaker phone IC 602 couples to hands-free microphone 50, via amplifier 604 and to hands-free speaker 52 via amplifier 606. Speaker phone IC 602 also drives cradle speaker 30a via amplifier 608 and monitors cradle microphone 30b via amplifier 610. Thus, speaker phone IC 602 is integrated into the circuitry of speaker driver 202.

Cradle speaker 30a and cradle microphone 30b may be replaced by a direct connection, with appropriate intervening coupling transformer, to the telephone line 38 as an alternative to acoustic coupling of patient telephone 36. It will be understood, therefore, that reference herein to cradle 30 also represents reference to a direct coupling between pacemaker monitor transmitter 10 and patient telephone line 38.

Speaker phone IC 602 is a voice-switched device. Generally, IC 602 couples in one mode the hands-free microphone 50 to cradle speaker 30a, and in a second mode couples cradle microphone 30b to the hands-free speaker 52. Thus, while in hands-free mode, speaker phone IC 602 allows patient 14 to speak to recipient 16 by way of hands-free microphone 50 and cradle speaker 30a. Recipient 16 speaks to patient 14 by way of cradle microphone 30b and hands-free speaker 52. As may be appreciated, only one of patient 14 and recipient 16 talk at a given time on the telephone connection, as orchestrated by speaker phone IC 602.

When not operating in hands-free mode, microcontroller 200 drives cradle speaker 30a as described herein above through appropriate filter and level adjust circuitry 612 as described herein above in connection with speaker driver 202. Further, microcontroller 200 monitors incoming DTMF commands by way of cradle microphone 30b and DTMF detector block 204. In this manner, microcontroller 200 selectively enters one of a hands-free mode or a normal operation mode. In accordance with a preferred form of the present invention, the hands-free mode of operation may be initiated through appropriate DTMF commands originating from recipient 16. Thus, recipient 16 may shut down operation of EKG signal transmission and speak directly to patient 14 by commanding pacemaker monitor transmitter 10 to enter hands-free mode and thereby establish a voice interaction with patient 14 by way of speaker phone IC 602.

Thus, an improved pacemaker monitor transmitter has been shown and described. The pacemaker monitor transmitter of the present invention converts EKG signals directly into digital form, and thereby advantageously provides digital signal procession algorithms thereto. Further, the hands-free operation of the device of the present invention facilitates more convenient execution of a heart and pacemaker monitoring session. Patient alert steps include, in addition to conventional alarm and flashing light, an ability of the recipient to interact verbally with the patient without requiring the patient to lift the telephone from the handset. Overall, the patient experiences less anxiety and stress because the recipient 16 can always interact verbally with patient 14 without requiring patient 14 to manipulate the pacemaker monitor transmitter 10.

It will be appreciated that the present invention is not restricted to the particular embodiment that has been described and illustrated, and that variations may be made therein without departing from the scope of the invention as found in the appended claims and equivalents thereof.

What is claimed is:

1. A pacemaker monitor transmitter device for coupling to a patient having a pacemaker and interacting with a remote station including a remote operator, the device comprising:

a telephonic communication channel delivering a pacemaker monitor transmitter device generated signal and a patient voice signal into a telephone connection and receiving from said telephone connection a remote signal including a command signal and a remote operator voice signal;

an electrode pair attachable to said patient and providing a patient signal; and a patient signal processing element receiving said patient signal in analog form, converting said patient signal to digital form, and providing said patient signal to said telephonic channel in frequency modulated form as said device generated signal.

2. A device according to claim 1 wherein said telephonic communication channel includes at least one of a cradle receiving a patient telephone handset and acoustic coupling to said patient telephone handset, a hands-free microphone monitoring said patient voice and producing said patient voice signal, a hands-free speaker providing to said patient acoustic representation of said remote operator voice signal, and conductors coupled directly to a telephone line jack.

3. A device according to claim 1 wherein said frequency modulated form is a function of a finite impulse response algorithm.

4. A device according to claim 1 wherein said processing element in converting said patient signal to digital form includes at least one digital signal processing function applied thereto.

5. A device according to claim 4 wherein said at least one digital signal processing function includes a finite impulse response function.

6. A device according to claim 1 wherein said command signal includes at least one of speaker volume increase, speaker volume decrease, toggle a pulse width component of said patient signal, patient alert, and toggle hands-free mode.

7. A device according to claim 1 wherein said patient signal as provided to said telephonic communication signal is a digitally generated tone.

8. A device according to claim 1 wherein said device further includes a command interface receiving from said remote operator a command signal and reacts to said command signal.

9. A pacemaker monitor transmitter device comprising:

a microcontroller;

a telephonic communication channel coupled to said microcontroller whereby said device applies signals, including patient voice signals, to a telephone connection and receives signals, including remote operator signals, from said telephone connection;

a patient signal interface including an electrode pair producing an analog patient signal and delivering said patient signal to said microcontroller whereby said microcontroller converts said patient signal to digital form, applies digital signal processing to said patient signal, and delivers said patient signal to said telephonic communication channel as digitally generated tones; and a command signal interface coupling said microcontroller and said telephonic communication channel whereby said microcontroller responds to signals received from said telephonic communication signal and reacts thereto.

10. A device according to claim 9 wherein said patient signal as delivered to said telephonic communication channel includes at least one of EKG signal representation and pacemaker stimulation pulse width representation.

11. A device according to claim 9 wherein said digital signal processing includes a finite impulse response function.

12. A method of monitoring patient heart and pacemaker condition comprising the steps:

coupling at a patient location said patient to electrodes and producing an analog patient signal;

receiving at said patient location said analog patient signal at a microcontroller and converting said analog patient signal into a digital patient signal;

providing at said patient location digitally generated tones representing said digital patient signal to a telephone connection;

monitoring at a remote station connected to said telephone connection said digitally generated tones;

providing at said remote station command signals introduced into said telephone connection; and monitoring at said patient location said command signals and reacting thereto, said monitoring and reacting step including a selected one of said command signals causing cessation of said digital patient signal and allowing bi-directional voice communication on said telephone connection between said patient and an operator at said remote station.

13. A pacemaker monitor transmitter device for coupling to a patient having a pacemaker and interacting with a remote station including a remote operator, the device comprising:

a telephonic communication channel delivering a pacemaker monitor transmitter device generated signal and a patient voice signal into a telephone connection and receiving from said telephone connection a remote signal including a command signal and a remote operator voice signal, said telephonic communication channel including a patient hands-free mode of operation with respect to said patient voice signal presentation to said remote operator and said remote operator voice signal presentation to said patient, said command signal including ability to cease delivery of said pacemaker monitor transmitter device generated signal and establish said hands-free mode of operation whereby said patient and said remote operator may interact verbally through said telephonic communication channel;

an electrode pair attachable to said patient and providing a patient signal; and a patient signal processing element receiving said patient signal and providing said patient signal to said telephonic channel as said device generated signal except when said hands-free mode is established by said command signal.

* * * * *